US009986751B2

(12) United States Patent
Bruins et al.

(10) Patent No.: US 9,986,751 B2
(45) Date of Patent: Jun. 5, 2018

(54) USE OF ASPERGILLUS NIGER ASPERGILLOGLUTAMIC PEPTIDASE TO IMPROVE ANIMAL PERFORMANCE

(71) Applicants: DSM IP ASSETS B.V., Heerlen (NL); NOVOZYMES A/S, Bagsvaerd (DK)

(72) Inventors: Maaike Johanna Bruins, Kaiseraugst (CH); Luppo Edens, Kaiseraugst (CH); Helena Maria Nan, Kaiseraugst (CH)

(73) Assignees: DSM IP ASSETS B.V., Heerlen (NL); NOVOZYMES A/S, Bagsvaerd (DK)

( * ) Notice: Subject to any disclaimer, the term of this patent is extended or adjusted under 35 U.S.C. 154(b) by 67 days.

(21) Appl. No.: 15/102,037

(22) PCT Filed: Dec. 11, 2014

(86) PCT No.: PCT/EP2014/077353
§ 371 (c)(1),
(2) Date: Jun. 6, 2016

(87) PCT Pub. No.: WO2015/086735
PCT Pub. Date: Jun. 18, 2015

(65) Prior Publication Data
US 2016/0302446 A1 Oct. 20, 2016

(30) Foreign Application Priority Data
Dec. 11, 2013 (EP) ..................................... 13196583

(51) Int. Cl.
| | |
|---|---|
| *A23K 20/189* | (2016.01) |
| *A23K 20/174* | (2016.01) |
| *A23K 10/14* | (2016.01) |
| *A23K 20/20* | (2016.01) |
| *A23K 50/75* | (2016.01) |
| *A23K 50/30* | (2016.01) |
| *A61K 38/48* | (2006.01) |

(52) U.S. Cl.
CPC ............ *A23K 20/189* (2016.05); *A23K 10/14* (2016.05); *A23K 20/174* (2016.05); *A23K 20/30* (2016.05); *A23K 50/30* (2016.05); *A23K 50/75* (2016.05); *A61K 38/488* (2013.01); *C12Y 304/23019* (2013.01)

(58) Field of Classification Search
None
See application file for complete search history.

(56) References Cited

U.S. PATENT DOCUMENTS

2003/0021774 A1  1/2003  Sjoeholm et al.
2008/0044501 A1  2/2008  Lee et al.

FOREIGN PATENT DOCUMENTS

WO   WO 95/28850      11/1995
WO   WO 2014/026981   2/2014

OTHER PUBLICATIONS

GRAS Notification for Carboxypeptidase from a Genetically Modified Strain of Aspergillus Niger, Jun. 24, 2010.*
International Search Report for PCT/EP2014/077353 dated Mar. 16, 2015, 4 pages.
Written Opinion of the ISA for PCT/EP2014/077353 dated Mar. 16, 2015, 5 pages.
Khuseeba Munir et al., "A review on role of exogenous enzyme supplementation in poultry production", *Emirates Journal of Food and Agriculture*, vol. 25, No. 1, Nov. 24, 2012, 15 pages.
Takahashi et al., "Aspergillopepsin II", *Handbook of Proteolytic Enzymes*, Jan. 1, 2004, pp. 221-224.

* cited by examiner

*Primary Examiner* — Suzanne M Noakes
*Assistant Examiner* — Stephen M Chong
(74) *Attorney, Agent, or Firm* — Nixon & Vanderhye P.C.

(57) ABSTRACT

This invention relates to the use of the *Aspergillus niger* aspergilloglutamic peptidase in a feed composition containing cereals, pulses, oilseeds, and/or tubers to improve animal performance, reduce nitrogen excretion and/or reduce intestinal inflammation. Furthermore, the present invention relates to a feed composition or a feed additive comprising the *Aspergillus niger* aspergilloglutamic peptidase. The present invention relates to the discovery that the *Aspergillus niger* aspergilloglutamic peptidase is capable of efficiently hydrolyzing alpha-amylase/trypsin inhibitors that are present in wheat, barley and related cereal species, as well as hydrolyzing trypsin inhibitors that are present in pulses, oilseeds, and tubers. Furthermore, the present invention relates to a method of improving animal performance comprising improving feed conversion ratio, and/or improving daily weight gain, and/or reducing intestinal inflammation, and/or reducing nitrogen excretion in an animal fed a feed stuff containing alpha-amylase and/or trypsin inhibitors, comprising orally administering a sufficient amount of the *Aspergillus niger* aspergilloglutamic peptidase. It also relates to the pretreatment of feedstuff with the *Aspergillus niger* aspergilloglutamic peptidase.

3 Claims, 4 Drawing Sheets

Figure 1:
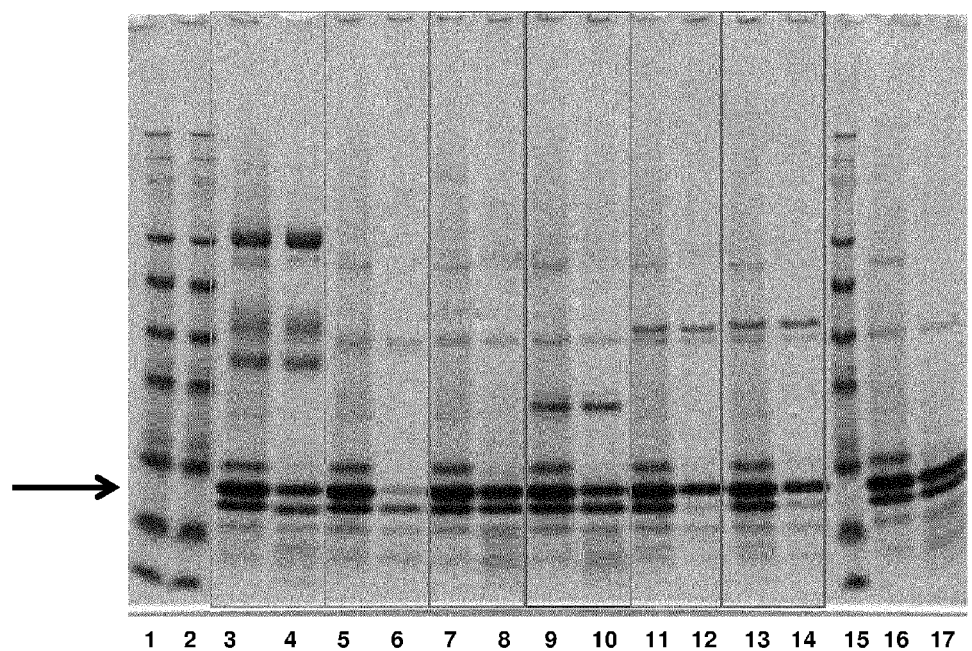

USE OF *ASPERGILLUS NIGER* ASPERGILLOGLUTAMIC PEPTIDASE TO IMPROVE ANIMAL PERFORMANCE

This application is the U.S. national phase of International Application No. PCT/EP2014/077353 filed 11 Dec. 2014 which designated the U.S. and claims priority to EP 13196583.2 filed 11 Dec. 2013, the entire contents of each of which are hereby incorporated by reference.

BRIEF DESCRIPTION OF THE INVENTION

This invention relates to the use of the *Aspergillus niger* aspergilloglutamic peptidase in a feed composition containing cereals, pulses, oilseeds, and/or tubers to improve animal performance, reduce nitrogen excretion, and/or improve protein digestibility. Furthermore, the present invention relates to a feed composition or a feed additive comprising the *Aspergillus niger* aspergilloglutamic peptidase. The present invention relates to the discovery that the *Aspergillus niger* aspergilloglutamic peptidase is capable of efficiently hydrolyzing alpha-amylase/trypsin inhibitors that are present in wheat, barley and related cereal species, as well as hydrolyzing trypsin inhibitors that are present in pulses, oilseeds, and tubers. Furthermore, the present invention relates to a method of improving animal performance comprising improving feed conversion ratio, and/or improving daily weight gain, and/or reducing intestinal inflammation, and/or reducing nitrogen excretion, and/or improving protein digestion in an animal fed a feed stuff containing alpha-amylase and/or trypsin inhibitors, comprising orally administering a sufficient amount of the *Aspergillus niger* aspergilloglutamic peptidase. It also relates to the pretreatment of feedstuff with the *Aspergillus niger* aspergilloglutamic peptidase. The present invention further relate to a feed composition comprising the *Aspergillus niger* aspergilloglutamic peptidase for use in reducing animal intestinal inflammation.

BACKGROUND OF THE INVENTION

Proteins are essential nutrients for animals and humans. Most livestock and humans get a large part of the necessary proteins from vegetable protein sources. Important vegetable protein sources are e.g. oilseed crops, legumes and cereals. When e.g. soybean meal is included in the feed of mono-gastric animals such as pigs and poultry, a significant proportion of the soybean meal solids is not digested. E.g., apparent ileal protein digestibilities of only 77% and 84% have been reported in piglets and growing pigs, respectively.

Indeed, cereal grains, pulses, and tubers contain a number of anti-nutritional factors and potential allergens such as alpha-amylase/trypsin inhibitors present in wheat, barley and related cereals, or soybean trypsin inhibitors (Kunitz type inhibitors and/or Bowman-Birk inhibitors) which prevent optimal growth performance, may alter health of the animal, and lead to an unnecessary release of nitrogen in the environment.

Most plant storage organs such as seeds and tubers contain 1-10% of their total proteins as protease inhibitors with different biochemical and structural properties inhibiting different types of proteases. Protein inhibitors are classified based on the type of enzyme they inhibit: serine protease inhibitors, cysteine protease inhibitors, aspartic protease inhibitors, or metallocarboxy-protease inhibitors.

Plant allergens are a widespread group of plant proteins comprising cupin and prolamin super families as well as proteinaceous molecules of the plant defense system. The prolamin superfamily includes several important types of allergens of legumes, tree nuts, cereals, fruits, and vegetables, and the cereal alpha-amylase and protease inhibitors. Based on structural similarity, proteinaceous alpha-amylase inhibitors with plant origin are usually classified in six families including lectin-like, knottin-like, CM-proteins, Kunitz-like, c-purothionin-like, and thaumatin-like (Richardson, 1991). CM (Chloroform-methanol)-proteins are a large protein family from cereal seeds containing 120 to 160 amino acid residues and five disulfide bonds. They show a typical double-headed alpha-amylase/trypsin domain. This feature makes it possible that they inhibit the activity of alpha-amylase and trypsin-like enzymes. The alpha-amylase inhibitor 0.19 is one of the most studied inhibitor of this family; it has a broad specificity, and inhibits alpha-amylases from insects, birds and mammals. Soybean trypsin inhibitor (Kunitz type) has first been discovered by Kunitz in 1945.

WO 2011/137322 recently disclosed that members of the alpha-amylase/trypsin inhibitor family contained in wheat and related cereals are strong inducers of innate immune response in human intestine. In farm animal, this effect translates into suboptimal animal performance, reduced digestibility, and intestinal inflammation.

The use of exogenous enzymes in animal feed has been one of the most promising strategies for improving animal performance as summarized in a recent review by Munir and Maqsood, EJFA, 2013, 25:66-80.

WO 2011/137322 disclosed the use of antibodies against alpha-amylase CM 3 in order to treat celiac patients or food compositions, and considers the use of protease as an alternative. However, it is silent with regard to a specific enzyme to efficiently hydrolyze alpha-amylase/trypsin inhibitors or Soybean trypsin inhibitors in the gastrointestinal tract of animals with the aim to improve digestibility and animal performance.

It would be desirable to provide a safe, effective and cost competitive way to degrade alpha-amylase/trypsin inhibitors or cereals as well as trypsin inhibitors of pulses, oilseeds, and tubers in the gastro intestinal tract of farm animals fed compositions comprising such inhibitors in order to reduce intestinal inflammation, to reduce nitrogen excretion, and to improve animal performance.

DETAILED DESCRIPTION OF THE INVENTION

Surprisingly, the present inventors have found, that an enzyme the *Aspergillus niger* aspergilloglutamic peptidase has a great potential to hydrolyze plant allergens/anti-nutritional factors such as alpha-amylase and/or trypsin inhibitors in the gastro intestinal system of an animal thereby leading to an improved animal performance, to a reduction of nitrogen excretion, and to a reduction of intestinal inflammation.

The present invention thus relates to the use of the *Aspergillus niger* aspergilloglutamic peptidase in a feed composition containing cereals, pulses, oilseeds, and/or tubers for improving animal performance.

The *Aspergillus niger* aspergilloglutamic peptidase (AGP) formerly called aspergillopepsin II isolated from *Aspergillus niger* var. *macrosporus* (EC 3.4.23.19) is a unique protease belonging to the peptidase family A4. This enzyme is not homologous to the aspartic proteases belonging to peptidases of family A1, which are typical pepsin-type acid proteases, thus being insensitive to their specific inhibitors such as pepstatin A. Therefore this enzyme was also classified as a 'pepstatin-insensitive' acid proteinase. Among the glutamic peptidases so far known, AGP is characteristic in that it is the sole two-chain enzyme. The amino acid sequence of the enzyme has no homology with those of typical aspartic proteinases.

The term *Aspergillus niger* aspergilloglutamic peptidase according to the present invention includes enzymes having at least 70% identity to the amino acid sequence of the *Aspergillus niger* aspergilloglutamic peptidase (UniProtKB/Swiss-Prot identifier P24665), for instance an enzyme having at least 80, 85, 90, 95, 98, 99% identity to P24665. Most preferred homologous enzymes according to the present invention are scytalidoglutamis peptidase from *Scytalidium lignicolum*, acid peptidases B and C from *Crypphonectria parasitica*, and an acid protease from *Scierotina scierotiorum*.

The *Aspergillus niger* aspergilloglutamic peptidase as disclosed herein may be present in a pure form, or as a preparation comprising the *Aspergillus niger* aspergilloglutamic peptidase, wherein at least 40%, 50%, 60%, 70%, 80%, 90%, 95% or more of the protease activity is derived from the *Aspergillus niger* aspergilloglutamic peptidase, wherein the activity is expressed in HPU (Histidine Protease Units); One HPU is the amount of enzyme that hydrolyses an amount of haemoglobin per minute, giving a solution with an optical density at 275 nm equal to the optical density of a solution containing 1 µg L-tyrosine per mL in 0.1 mol/L HCl solution. Conditions of the test are: pH 1.75, temperature 40° C., haemoglobin concentration during incubation 16.7 g/L.

$$\text{Activity(HPU/mL)}=(OD_{sample}-OD_{blank}/S)\times 11/30$$

Wherein:

$OD_{sample}$: Optical density of the sample filtrate (275 nm)

$OD_{blank}$: Optical density of the sample blank filtrate (275 nm)

S: OD of a L-tyrosine standard solution of 1.1 µg/mL (mL/µg)

30: incubation time (minutes)

11: total volume reaction mixture (mL).

The *Aspergillus niger* aspergilloglutamic peptidase according to the present invention can be prepared as disclosed in Handbook of Proteolytic Enzymes, A. J. Barret, N. D. Rawlings, and J. F. Woessner eds.; Academic Press; or in PCT/EP2013/066899.

According to the present invention, the improved animal performance is characterized by an improved feed conversion ratio, an improved daily weight gain, an improved digestibility, a reduction of nitrogen excretion, and/or reduced intestinal inflammation. Animal performance can be assessed by methods well known in the art, and is usually characterized by feed conversion ratio, feed intake, digestibility, weight gain, carcass yield. Intestinal inflammation will lead to reduced feed intake, or reduced digestibility.

The term "animal" includes all animals, including human beings. Preferred animal according to the present invention is a monogastric animal (single-chambered stomach), more preferred is a monogastric animal selected from non-ruminant animals, particularly: pets (including but not limited to horses, cats and dogs), poultry (including but not limited to (turkeys, ducks and chickens), pig or swine (included but not limited to piglets, growing pigs, and sows), fish (including but not limited to salmon, trout, tilapia, catfish, and carp), and rabbit.

The term "feed" or "feed composition" means any compound, preparation, mixture, or composition suitable for, or intended for intake by an animal. In one embodiment, the feed has a content of energy (e.g. therapeutics are excepted). In another embodiment, one or more vegetable proteins are included in the feed. These may derive partly from legumes, e.g.: soybeans, beans, or peas, partly from cereals, e.g.: wheat, barley or maize, partly from oilseeds, e.g.: sunflower seed, or rapeseed, and/or partly from tubers e.g.: patatoes. In the use according to the invention the *Aspergillus niger* aspergilloglutamic peptidase can be fed to the animal before, after, or simultaneously with the diet. The latter is preferred.

The *Aspergillus niger* aspergilloglutamic peptidase should of course be applied in an effective amount, i.e. in an amount adequate for improving digestion and/or degradation of amylase/trypsin inhibitors, Kunitz inhibitors and/or Bowman-Birk inhibitors, thereby improving the nutritional value of feed. It is at present contemplated that the enzyme is administered in e.g. one or more of the following amounts: From about 0.01 mg to about 100 mg enzyme/kg animal feed; or preferably from about 0.05 mg to about 50 mg enzyme/kg animal feed, more preferably, from 0.1 to 10 mg enzyme/kg animal feed.

The normal daily dosage of an enzyme provided to an animal by feed intake depends upon the kind of animal and its condition and is easily adjusted by the person skilled in the art. For the use according to the present invention the feed comprises an amount of enzyme units of *Aspergillus niger* aspergilloglutamic peptidase per Kg of feed that is capable of digesting 60 to 95% of the alpha-amylase/trypsin inhibitors carried through the wheat, soy or related cereal. Preferably, the feed composition comprises 1 to 10,000 HPU/Kg of feed, more preferably, 10 to 5,000 HPU/Kg of feed, even more preferably, 50 to 1,000 HPU/Kg of feed.

The improved animal performance is preferably measured as improved feed conversion ratio, improved daily weight gain, improved digestibility, and/or reduced intestinal inflammation. The feed conversion ratio (FCR) may be determined on the basis of a standard animal growth trial comprising a first treatment in which enzyme is added to the animal feed in a suitable concentration per kg feed, and a second treatment (control) with no addition of the enzyme to the animal feed. The FCR is calculated as the feed intake in g/animal relative to the weight gain in g/animal. As it is generally known, an improved FCR is lower than the control FCR. More preferably for the present use, improved feed conversion ratio means a reduction by least 1% when measured in conventional animal performance trial. Preferably, the feed conversion ratio is reduced by at least 2%, more preferably, by at least 2.5%, even more preferably, by at least 3%, most preferably, by at least 3.5%.

For the realisation of the use of the *Aspergillus niger* aspergilloglutamic peptidase for the feed of animals, the enzyme may be incorporated in the feed by methods known per se in the art of feed formulation and processing. In a particular embodiment, the enzyme is formulated as an enzyme granule comprising a zinc salt of an organic acid, in order to make it resistant to steam pelleting as described in US 2008/0031998. Thus, the present invention relates to the use of the *Aspergillus niger* aspergilloglutamic peptidase in a feed composition containing wheat, barley, or soy for improving animal performance, wherein the *Aspergillus niger* aspergilloglutamic peptidase enzyme is in the form of a granule comprising a zinc salt of an organic acid. The zinc salt of an organic acid is in a particular embodiment water soluble. When working with feed for animals it is important that the materials used in the granule have a certain purity thus in one embodiment of the present invention the zinc salt of organic acid is food grade. The organic zinc salt of an organic acid may be selected but is not limited to the group consisting of zinc salts of citrate, malate, maleate, malonate, methionate, succinate, lactate, formate, acetate, butyrate, propionate, benzoate, tartrate, ascorbate, gluconate, zinc chelates of amino acids hydrates and combinations thereof.

In a particular embodiment of the present invention the zinc salt of an organic acid is selected from the group consisting of zinc salts of citrate, malate, maleate, malonate, methionate, succinate, lactate, formate, acetate and zinc chelates of amino acids hydrates. The zinc salt of an organic acid may be selected from the group consisting of zinc citrate, zinc malate, zinc maleate, zinc malonate, zinc methionate, zinc succinate, zinc lactate, zinc formate, zinc acetate, zinc butyrate, zinc propionate, zinc benzoate, zinc tatrate, zinc ascorbate, zinc gluconate, zinc methionate, zinc lysine, zinc methionine and combinations thereof. The zinc salt of an organic acid may be selected from the group consisting of zinc citrate, zinc malate, zinc maleate, zinc malonate, zinc methionate, zinc succinate, zinc lactate, zinc formate, zinc acetate, zinc butyrate, zinc propionate, zinc benzoate, zinc tatrate, zinc ascorbate, zinc gluconate, zinc methionate, zinc lysine and combinations thereof.

Furthermore, the feed composition according to the present invention may further comprise one or more additional exogenous enzymes selected from selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4), phospholipase A1 (EC 3.1.1.32); phospholipase A2 (EC 3.1.1.4); lysophospholipase (EC 3.1.1.5); phospholipase C (EC 3.1.4.3); phospholipase D (EC 3.1.4.4); amylase such as, for example, alpha-amylase (EC 3.2.1.1); and/or beta-glucanase (EC 3.2.1.4 or EC 3.2.1.6) or any mixture thereof.

Preferably, the feed composition or feed additive according to the present invention further comprise one or more additional exogenous enzyme selected from another protease (e.g.: RONOZYME-ProAct) and/or a phytase (e.g.: RONOZYME-Hiphos).

The present invention relates to the compositions and use of *Aspergillus niger* aspergilloglutamic peptidase Thus it specifically relates to a feed composition or a feed additive comprising *Aspergillus niger* aspergilloglutamic peptidase with the above embodiments. Preferably, the feed composition comprises 2 to 10,000 HPU/Kg of feed, more preferably, 10 to 5,000 HPU/Kg of feed, even more preferably, 50 to 1000 HPU/Kg of feed.

In all the embodiments according to the present invention, cereals are selected from wheat, barley, maize or rye, pulses are selected from soybeans, beans, or peas, oilseeds are selected from sunflower seed, or rapeseed, and tubers are patatoes. Preferably, cereals are selected from wheat, barley, maize, and, pulses are selected from soybeans. In the most preferred embodiments of the preferred invention, cereals are wheat and pulse is soybean.

Thus a preferred feed composition according to the present invention comprises cereals selected from wheat, barley, or maize, pulses selected from soybean, oilseeds, and/or tubers, more preferably, it comprises cereals selected from wheat, and pulses selected from soybean.

Particular examples of feed compositions of the invention are the following:

An animal feed additive comprising (a) *Aspergillus niger* aspergilloglutamic peptidase (b) at least one fat-soluble vitamin, (c) at least one water-soluble vitamin, and/or (d) at least one trace mineral;

An animal feed composition comprising *Aspergillus niger* aspergilloglutamic peptidase and a crude protein content of 50 to 800 g/kg feed.

An animal feed composition comprising *Aspergillus niger* aspergilloglutamic peptidase and a cereal selected from wheat, barley, or related cereal species. Preferably, said feed composition comprises 5 to 60 wt.-% of a cereal selected from wheat, barley, or related cereal species, more preferably, it is wheat.

The so-called premixes are examples of animal feed additives of the invention. A premix designates a preferably uniform mixture of one or more micro-ingredients with diluent and/or carrier. Premixes are used to facilitate uniform dispersion of micro-ingredients in a larger mix.

In another embodiment, the present invention relates to the *Aspergillus niger* aspergilloglutamic peptidase for use in a feed composition containing wheat, barley, soy or related cereals for reducing intestinal inflammation in an animal.

In yet another embodiment, the present invention relates to a method of improving animal performance comprising improving feed conversion ratio, and/or improving daily weight gain, and/or reducing nitrogen excretion, and/or reducing intestinal inflammation in an animal fed cereals, pulses, oilseeds, and/or tubers, comprising orally administering a sufficient amount of the *Aspergillus niger* aspergilloglutamic peptidase. More preferably, cereals are selected form wheat or barley, and pulse is soybean; even more preferably, cereal is wheat and pulse is soybean.

In a further embodiment, the present invention relates to the use of the *Aspergillus niger* aspergilloglutamic peptidase for pre-treatment of animal feed or animal feed components containing cereals, pulses, oilseeds, and/or tubers. Preferably, cereals are selected form wheat or barley, and pulse is soybean; more preferably, cereal is wheat, and pulse is soybean. The person skilled in the art will estimate the amount of the *Aspergillus niger* aspergilloglutamic peptidase to be added to the feed, and the time required to degrade the protease inhibitors depending on the feed composition being treated. For wheat based feed, *Aspergillus niger* aspergilloglutamic peptidase is added at 50 to 5000 HPU/Kg of wheat, preferably 100 to 2000 HPU/Kg of wheat.

The plant allergens protease inhibitors degraded by the *Aspergillus niger* aspergilloglutamic peptidase according to the present invention are preferably those specifically found in wheat, barley, rye, oat and their cross-related varieties, such as alpha-amylase/trypsin inhibitors, more preferably, the plant allergens are CM 2, CM 3, CM 16, and 0.19, and even more preferably CM 3 and 0.19, on the basis of their rapid degradation by the *Aspergillus niger* aspergilloglutamic peptidase. CM 3 amino acid sequence identifier is SwissProt P01083, while 0.19 amino acid sequence identifier is Swiss Prot P01085. Moreover, soybean proteinase inhibitors of the Kunitz type (Swiss Prot ID: P01070) and Bowman-Birk type (Swiss Prot ID: P01055) are also efficiently degraded by the *Aspergillus niger* aspergilloglutamic peptidase, thereby contributing to the improvement of the animal performance.

Preferred amount of enzyme to be added to the feed composition in the above method is dependent on the feed matrix and the estimated amount of alpha-amylase/trypsin inhibitor.

In yet another embodiment, the present invention relates to a feed prepared by the method above for degrading amylase/protease inhibitors in a feed composition comprising, incubating a feed composition containing plant allergens/protease inhibitors with *Aspergillus niger* aspergilloglutamic peptidase, for a time sufficient to hydrolyze plant allergens/protease inhibitors, said feed composition comprising degraded alpha-amylase/trypsin inhibitors.

In yet another embodiment, the present invention relates to the use of the *Aspergillus niger* aspergilloglutamic peptidase with all the embodiments above in a food composition containing cereals, pulses, oilseeds, and/or tubers for improving protein digestibility in human.

In yet another embodiment, the present invention relates to the use of the *Aspergillus niger* aspergilloglutamic peptidase for pre-treatment of a food or foodstuff containing cereals, pulses, oilseeds, and/or tubers so as to prevent heat pretreatment during processing. Preferred foodstuff is soybean containing food ingredient.

FIGURE LEGENDS

FIG. 1: 4-12% SDS-PAGE (4 to 12% Bis-Tris gel) analysis of various incubations of wheat alpha amylase inhibitors with different proteases plus pepsin under simulated stomach conditions. Two controls with pepsin treatment without additional enzyme are included. The arrow indicates the position of the three major protein products present in the alpha amylase preparation.
  Molecular weight markers: lanes 1, 2, and 15
  *A. niger* proline-specific endoprotease treatment at: t=0, lane 3; t=90 minutes, lane 4
  *A. niger* aspergilloglutamic peptidase at: t=0, lane 5; t=90 minutes, lane 6
  Pepsin at: t=0, lane 7; t=90 minutes, lane 8
  Papain at: t=0, lane 9; t=90 minutes, lane 10
  Multifect PR 15 L at: t=0, lane 11; t=90 minutes, lane 12
  Aspergillopepsin I at: t=0, lane 13; t=90 minutes, lane 14
  Pepsin at: t=0, lane 16; t=90 minutes lane 17.

Figure 2:
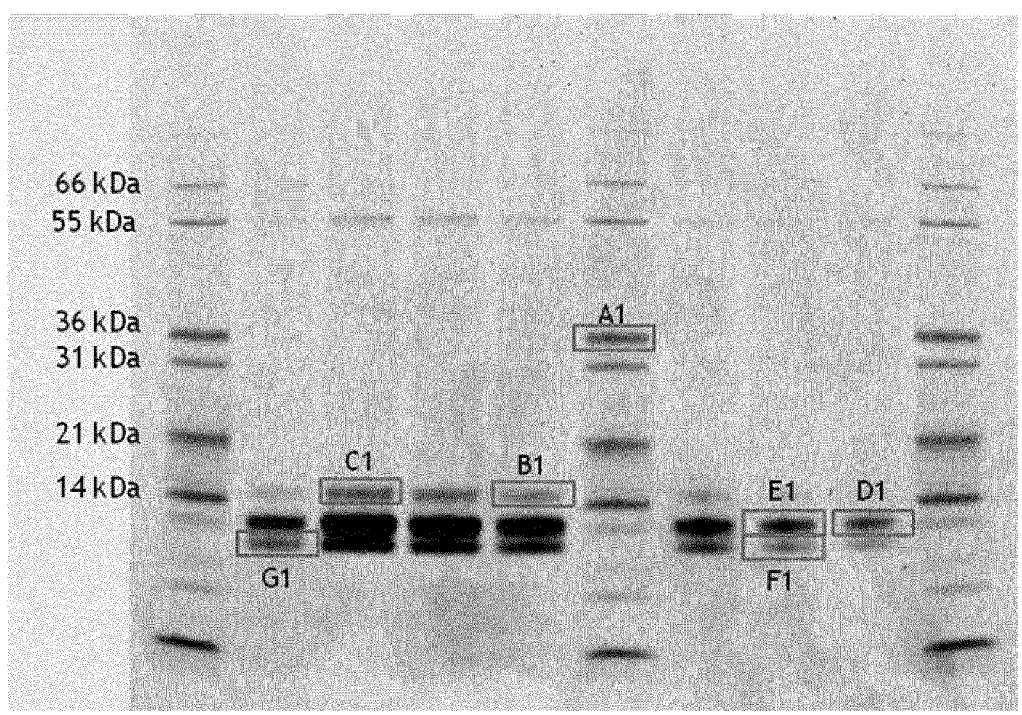

FIG. 2: Preparative SDS-PAGE of wheat alpha amylase inhibitors to identify the nature of the most abundant proteins present in bands B1 to G1.

Figure 3:
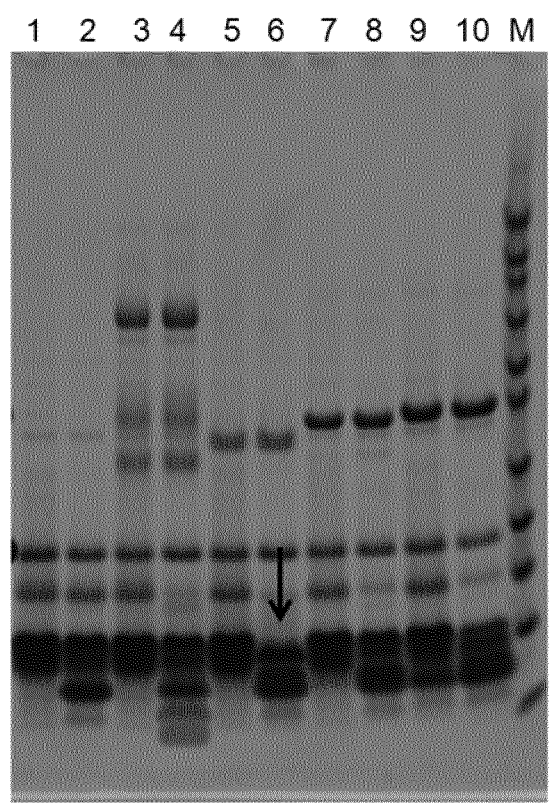

FIG. 3: 4-12% SDS-PAGE (4 to 12% Bis-Tris gel) analysis of various incubations of soybean derived trypsin-chymotrypsin inhibitors with different proteases plus pepsin under simulated stomach conditions. A control with pepsin treatment without additional enzyme is included. The arrow indicates the position of the upper major protein product present in the soybean derived trypsin-chymotrypsin inhibitor that is degraded.
  Molecular weight markers: lane M
  Pepsin at: t=0, lane 1; t=60 minutes, lane 2
  *A. niger* proline-specific endoprotease at: t=0, lane 3; t=60 minutes, lane 4
  *A. niger* aspergilloglutamic peptidase at: t=0, lane 5; t=60 minutes, lane 6
  Multifect PR 15 L at: t=0, lane 7; t=60 minutes, lane 8
  Aspergillopepsin I at: t=0, lane 9; t=60 minutes, lane 10

Figure 4:
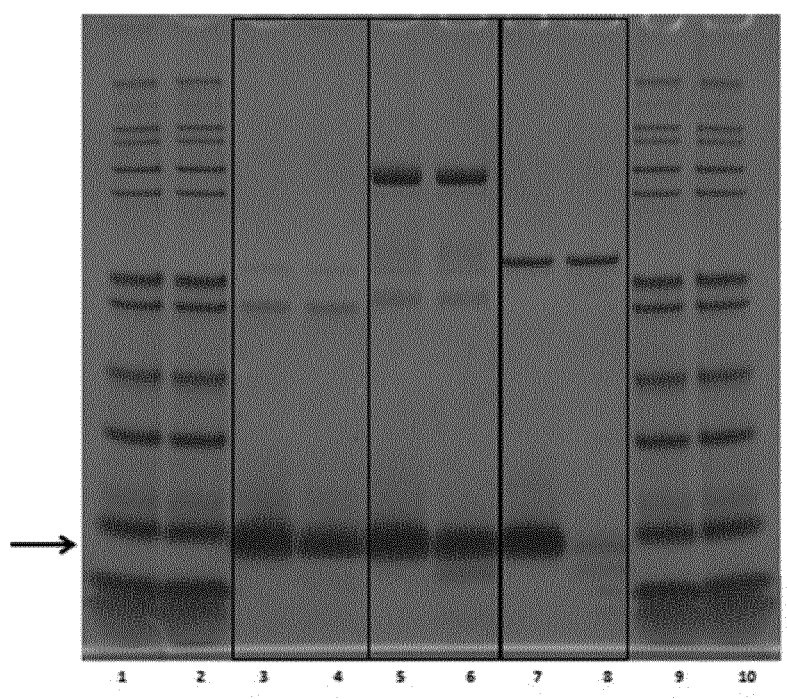

FIG. 4: 4-12% SDS-PAGE (4 to 12% Bis-Tris gel) analysis of various incubations of wheat derived purothionins with different proteases plus pepsin under simulated stomach conditions. The arrow indicates the position of the purified purothionins.
  Molecular weight markers: lanes 1, 2, 9 and 10
  *A. niger* aspergilloglutamic peptidase at: t=0, lane 3; t=90 minutes, lane 4
  *A. niger* proline-specific endoprotease at: t=0, lane 5; t=90 minutes, lane 6
  Multifect PR 15 L (aspergillopepsin I-like protease from *Trichoderma reesei*) at: t=0, lane 7; and t=90 minutes, lane 8.

The invention is further illustrated by the following examples.

EXAMPLES

Example 1

*Aspergillus niger* Aspergilloglutamic Peptidase Efficiently Cleaves Wheat Derived Alpha Amylase/Trypsin Inhibitors Under Simulated Stomach Conditions, While Other Acidic Endoproteases are not Efficient Materials & Methods
Production of Aspergillopepsin I from *Aspergillus niger*

The gene for aspergillopepsin I from *Aspergillus niger* (pepA; An14g04710) was over-expressed in an *A. niger* host using methods such as described in WO 98/46772. WO 98/46772 discloses how to select for transformants on agar plates containing acetamide, and to select targeted multi-copy integrants. *A. niger* transformants containing multiple copies of the expression cassette were selected for further generation of sample material. The transformed *A. niger* strain was fermented in a modified CSM-fermentation medium, pH 6.2 (40 g/l Maltose, 30 g/l Bacto-soytone, 70 g/l Sodium citrate tribasic dihydrate, 15 g/l $(NH_4)_2SO_4$, 1 g/l $NaH_2PO_4*2H_2O$, 1 g/l $MgSO_4*7H_2O$, 1 g/l L-Arg, 0.25 ml/l Clerol Antifoam). The culture broth obtained was filtered, sterile filtered and then concentrated by ultrafiltration. Chromatography was carried out by applying the enzyme to a Q-sepharose XK 26/10 column in 50 mmol/l Na-acetate, pH 5.6, followed by elution with a salt gradient. The presence of the aspergillopepsin I protein in the various fractions was quantified by judging the intensity of coloured protein bands after 4-12% SDS-PAGE (NuPAGE Bis-Tris Gel, Invitrogen).

Enzymatic Assay

Incubations were carried out in 50 mmol/l Na citrate at pH 4.0 for 90 minutes at 37° C. In all relevant incubations pepsin was present in an enzyme protein concentration of 0.2 mg/ml. The proline-specific endoproteinase was tested in a concentration of 0.5 mg enzyme protein/ml, the other acid endoproteinases in a concentration of 0.05 mg enzyme protein/ml. The amylase inhibitor was added last and present in a concentration of 2 mg/ml.

At t=0, 100 microliter of the reaction mixture was transferred into 400 microliter 25% TCA. After 90 minutes of incubation at 37° C., another 100 microliter was transferred into 400 microliter of fresh TCA solution. After 2 hours at 4° C., the samples were centrifuged for 10 minutes at 14,000 rpm. After centrifugation, 65 microliter of phosphate buffer pH 7, 25 microliter of lithium dodecyl sulfate (LiDS) and 10 microliter of sample reducing agent were added. The samples were stored at 4° C. overnight and then prepared for SDS-PAGE following the Invitrogen protocol (Invitrogen, www.lifetechnologies.com)

Determination of *A. niger* Aspergilloglutamic Peptidase Activity (HPU)

20.0 g haemoglobin from bovine blood (Sigma product H2625) was suspended in approximately 700 mL water by stirring for 10 minutes at room temperature. After the addition of 3.73 g potassium chloride (KCl) the pH was adjusted to 1.75 with 0.5 mol/L hydrochloric acid. The volume of the haemoglobin suspension was adjusted to 1 L with water. The pH was checked again and adjusted to pH 1.75.

Enzyme solutions were prepared by dissolving purified aspergilloglutamic peptidase produced as disclosed above in a KCl/HCl buffer containing 3.73 g/l KCl adjusted to pH 1.75 with 2.0 mol/L HCl. To test aspergilloglutamic peptidase activity, 5 ml of the haemoglobin solution was heated at 40° C. and subsequently 1 mL enzyme solution with an activity between 5 and 25 Histidine Protease Units (HPU/mL) was added to start the reaction. After 30 minutes the reaction was stopped by adding 5 mL trichloro acetic acid solution (140 g/L) to precipitate larger peptide fragments. A blank measurement was done by adding 1.0 mL enzyme sample to a mixture of 5 mL haemoglobin solution and 5 mL trichloro acetic acid solution. The tubes were incubated at 40° C. for 30 minutes to complete the precipitation. After centrifugation, the optical density of the clear supernatant containing small peptides was measured at 275 nm. The result was compared to an L-tyrosine solution of 1 µg/mL.

One HPU is the amount of enzyme that hydrolyzes an amount of haemoglobin per minute, giving a solution with an optical density at 275 nm equal to the optical density of a solution containing 1 µg L-tyrosine per mL in 0.1 mol/L HCl solution. Conditions of the test are: pH 1.75, temperature 40° C., haemoglobin concentration during incubation 16.7 g/L.

Activity (HPU/mL)=($OD_{sample}$−$OD_{blank}$/S)×11/30

Where:
$OD_{sample}$: Optical density of the sample filtrate (275 nm)
$OD_{blank}$: Optical density of the sample blank filtrate (275 nm)
S: OD of a L-tyrosine standard solution of 1.1 µg/mL (mL/µg)
30: incubation time (minutes)
11: total volume reaction mixture (mL)

LC-MS/MS Analysis
In-vitro Digestion

The sample was dissolved to 1 mg/ml in MilliQ water. The solution was 10× diluted in 100 mM $NH_4HCO_3$ (pH7.8). The sample was reduced by addition of DTT, 5 mM, 30 minute incubation at room temperature and alkylated by addition of iodoacetamide (IAA), 5.5 mM, 30 minute incubation at room temperature in the dark. Digestion with trypsin was performed at 37° C. overnight.

In Gel Digestion

Gel bands were cut out of the gel using the ExQuest spot cutter (Biorad, Hercules, Calif., USA) and transferred into a lo-protein bind MTP (Eppendorf, Hamburg Germany). The gel pieces were washed by adding 75 µl 50 mM $NH_4HCO_3$ to swell and 75 µl Acetonitrile to shrink, total 3 washes. The washed gel pieces were digested with trypsin digestion was performed by incubation at 37° C. overnight. The samples were sonicated for 1 minute and the supernatant was collected into an injection-vial.

LC-MS/MS Analysis

The samples were acidified to 1% formic acid and analyzed on the Accela-LTQ-Velos (Thermo Scientific, San Diego, Calif. USA). The chromatographic separation was achieved with a 2.1×100 mm 1.8 micrometer particle size, 80 Å pore size, C-18 Eclipse XDB Zorbax column (Agilent Santa Clara, Calif. USA), using a gradient elution with (A) LC-MS grade water containing 0.1% formic acid B) LC-MS grade acetonitrile containing 0.1% formic acid solution (Biosolve BV, the Netherlands) as mobile phases. The gradient was from 5 to 40% B in 83 minutes. The flow rate was kept at 0.4 ml/min, using an injection volume of 25 µl and the column temperature was set to 50° C. MS data acquisition was performed using a top 10 data-dependent acquisition with mass range 400-2000 m/z, using Dynamic exclusion and including charge states 2 and 3 only. MS/MS experiments were performed with an isolation width set at 3.0, and the normalized collision energy was set to 35.

Database searches were performed using the Sorcerer 2 (Sorcerer™-SEQUEST®) search engine and the Trans Proteome Pipeline (TPP), using trypsin as preferred enzyme. Only proteins identified with a confidence >90% were considered. The data was searched against the Swissprot database.

Results

In the present Example we demonstrate (See FIG. 1) that, under simulated gastric conditions, only Aspergillus niger aspergilloglutamic peptidase among a number of acidic endoproteinases is capable to efficiently degrade a purified preparation incorporating various wheat alpha amylase inhibitors (alpha amylase inhibitor from wheat seed, Type 1, Sigma). In the experiment the efficacies of the following enzymes were compared in the presence of pepsin (control):
pepsin (porcine gastric mucosa, Sigma),
proline-specific endoproteinase from Aspergillus niger (MaxiPro PSP, DSM Food Specialities, Delft, The Netherlands)
papain (Collupuline, DSM Food Specialities, Delft, The Netherlands),
Aspergillus niger aspergilloglutamic peptidase also called aspergillopepsin II (MaxiPro HSP,DSM Food Specialities, Delft, The Netherlands),
aspergillopepsin I (see Materials & Methods),
Multifect PR 15 L (aspergillopepsin I-like protease from Trichoderma reesei; http//biosciences.dupont.com).

The results (cf. FIG. 1), show that the purified wheat gluten alpha amylase inhibitor preparation incorporates three major protein bands with a size of approximately 12 kDa (see arrow). These data also show that under simulated stomach conditions and in the presence of pepsin and equal amounts of the various proteinases, the Aspergillus niger aspergilloglutamic peptidase is most effective in degrading these three major bands present in a purified preparation of alpha amylase inhibitors.

To confirm the nature of the different proteins present in each one of these bands, samples of gel bands were cut out, extracted and the proteins present were identified using LC-MS/MS analysis as described in the Materials & Methods above.

In this case the 10 mg/ml of the Sigma alpha amylase inhibitor solution was diluted 10 times with water. Then 65 microliter of this solution was mixed with 25 microliter of LiDS sample buffer and 10 microliter of the sample reducing agent, heated for 10 minutes at 70° C., after which the proteins were separated by SDS-PAGE according to the Invitrogen protocol. Then the gel was fixed for 1 hour with 50% methanol/7% acetic acid, rinsed twice with demineralized water and stained with Sypro Ruby overnight. Gel samples were obtained of the three, presumably alpha amylase inhibitor, bands as illustrated in FIG. 2. According to the LC-MS/MS data obtained from the extracted proteins, the most abundant proteins present in bands C1 and B1 are wheat alpha amylase inhibitors with the SwissProt accession numbers P17314 (CM 3) and P16159 (CM 16), in bands E1 and D1 the wheat alpha amylase inhibitors P01085 (0.19), P16851 (CM 2) and P16159 (CM 16) and in bands G1 and F1 P01083 (CM 3).

This data demonstrates that the Aspergillus niger aspergilloglutamic peptidase is surprisingly the most efficacious in degrading wheat derived alpha amylase inhibitors under stomach conditions and most notably, wheat alpha amylase inhibitors: CM 2, CM 3, CM 16, and 0.19.

Example 2

Animal Feed Additive

An animal feed additive is prepared by adding 100,000 HPU of *Aspergillus niger* aspergilloglutamic peptidase to the following premix (per kilo of premix):

| | | | |
|---|---|---|---|
| 1100000 IE | Vitamin A | 50004 mg | Cholin chloride |
| 300000 IE | Vitamin D3 | 6000 mg | Fe |
| 4000 IE | Vitamin E | 3000 mg | Cu |
| 250 mg | Vitamin B1 | 5400 mg | Zn |
| 800 mg | Vitamin B2 | 8000 mg | Mn |
| 1200 mg | Ca-D-Panthothenate | 124 mg | I |
| 500 mg | Vitamin B6 | 60 mg | Co |
| 2.5 mg | Vitamin B12 | 29.7 mg | Se |
| 5000 mg | Niacin | 9000 mg | Lasalocid Sodium (Avatec) |
| 10000 mg | Vitamin C | 17.3% | Ca |
| 300 mg | Vitamin K3 | 0.8% | Mg |
| 15 mg | Biotin | 11.7% | Na |
| 150 mg | Folic acid | | |

Example 3

Animal Feed

A broiler grower diet having the following composition (%, w/w) is prepared by mixing the ingredients. Wheat, rye and SBM 48 are available from Moulin Moderne Hirsinque, Hirsingue, France. After mixing, the feed is pelleted at a desired temperature, e.g. about 70° C. (3×25 mm).

| | |
|---|---|
| Wheat | 46.00 |
| Rye | 15.00 |
| Soy Bean Meal (SBM 48) | 30.73 |
| Soybean oil | 4.90 |
| DL-Methionine | 0.04 |
| DCP (Di-Calcium Phosphate) | 1.65 |
| Limestone | 0.43 |
| Salt | 0.15 |
| TiO2 | 0.10 |
| Animal feed additive (above) | 1.00 |

The resulting animal feed comprises 1000 HPU *Aspergillus niger* aspergilloglutamic peptidase per kg.

Example 4

Piglet Feed

A piglet feed containing *Aspergillus niger* aspergilloglutamic peptidase can be prepared by mixing the following ingredients together using a conventional mixing apparatus at room temperature.

| Ingredient | Amount (Weight %) |
|---|---|
| Wheat | 32.6 |
| Maize | 18.7 |
| Rice | 5.0 |
| Wheat bran | 9.0 |
| Soybean meal | 23.0 |
| Soy oil | 2.0 |
| Wheat starch | 4.5 |
| Minerals* | 2.9 |
| Synthetic amino acids premix** | 0.8 |
| Vitamins and trace elements premix*** | 1.0 |
| *Aspergillus niger* aspergilloglutamic peptidase premix (10% in wheat starch) | 0.5 |

In principle the *Aspergillus niger* aspergilloglutamic peptidase premix may contain 1-20% of the *Aspergillus niger* aspergilloglutamic peptidase.
*Sea salt, dicalcium phosphate and calcium carbonate;
**Lysine, methionine and threonine;
***Vitamins A, E, D3, K3, B1, B2, B6, B12, C, biotin, folic acid, niacin, pantothenic acid, choline chloride, copper sulphate, iron sulphate, manganese oxide, zinc oxide, cobalt carbonate, calcium iodide and sodium selenite.

Example 5

Growing Pig Feed

A growing pig feed containing *Aspergillus niger* aspergilloglutamic peptidase can be prepared by mixing the following ingredients together using a conventional mixing apparatus at room temperature.

| Ingredient | Amount (Weight %) |
|---|---|
| Soybean meal | 18.0 |
| Maize | 52.3 |
| Barley | 13.0 |
| Oat meal | 6.0 |
| Wheat bran | 5.2 |
| Soy oil | 2.0 |
| Minerals* | 1.5 |
| Synthetic amino acids premix** | 0.5 |
| Vitamins and trace elements premix*** | 1.0 |
| *Aspergillus niger* aspergilloglutamic peptidase premix (10% in wheat starch) | 0.5 |

Example 6

Broiler Chicken Starter Feed

A broiler chicken feed ("starter") containing *Aspergillus niger* aspergilloglutamic peptidase can be prepared by mixing the following ingredients together using a conventional mixing apparatus at room temperature.

| Ingredient | Amount (Weight %) |
|---|---|
| Soybean meal | 34.50 |
| Maize | 20.00 |
| Wheat | 37.80 |
| Soy oil | 3.13 |
| Minerals* | 2.90 |
| Synthetic amino acids premix** | 0.17 |
| Vitamins and trace elements premix*** | 1.00 |
| *Aspergillus niger* aspergilloglutamic peptidase premix (10% in wheat starch) | 0.50 |

Example 7

Broiler Chicken Grower Feed

A broiler chicken food ("grower") containing *Aspergillus niger* aspergilloglutamic peptidase can be prepared by mixing the following ingredients together using a conventional mixing apparatus at room temperature.

| Ingredients | Amount (Weight %) |
| --- | --- |
| Soybean meal | 31.2 |
| Maize | 20.0 |
| Wheat | 41.3 |
| Soy oil | 3.4 |
| Minerals* | 2.5 |
| Synthetic amino acids premix** | 0.1 |
| Vitamins and trace elements premix*** | 1.0 |
| *Aspergillus niger* aspergilloglutamic peptidase premix (10% in wheat starch) | 0.5 |

Example 8

*Aspergillus niger* Aspergilloglutamic Peptidase Efficiently Cleaves Soybean Derived Trypsin-Chymotrypsin Inhibitors Under Simulated Stomach Conditions, While Other Acidic Endoproteases are not Efficient Materials & Methods
Enzymatic Assay Incubations were carried out in 50 mmol/l Na citrate at pH 4.0 for 60 minutes at 37° C. In all relevant incubations pepsin was present in an enzyme protein concentration of 0.2 mg/ml. All peptidases were tested in a concentration of 0.5 mg enzyme protein/ml. The trypsin-chymotrypsin inhibitors inhibitor (purchased from Sigma T9777) was added last and present in a concentration of 2 mg/ml.

At t=0, 100 microliter of the reaction mixture was transferred into 400 microliter 25% TCA. After 60 minutes of incubation at 37° C., another 100 microliter was transferred into 400 microliter of fresh TCA solution. After 18 hours at 4° C., the samples were centrifuged for 30 minutes at 14,000 rpm. After centrifugation, 65 microliter of phosphate buffer pH 7, 25 microliter of lithium dodecyl sulfate (LiDS) and 10 microliter of sample reducing agent were added and prepared for SDS-PAGE following the Invitrogen protocol (Invitrogen, www.lifetechnologies.com)
Results In the present Example we demonstrate that, under simulated gastric conditions, only *Aspergillus niger* aspergilloglutamic peptidase among a number of acidic endoproteinases is capable to efficiently degrade a purified preparation incorporating Trypsin-Chymotrypsin from soybean, Sigma). In the experiment the efficacies of the following enzymes were compared in the presence of pepsin (control):

pepsin (porcine gastric mucosa, Sigma),
proline-specific endoproteinase from *Aspergillus niger* (MaxiPro PSP, DSM Food Specialities, Delft, The Netherlands)
*Aspergillus niger* aspergilloglutamic peptidase also called aspergillopepsin II (MaxiPro HSP, DSM Food Specialities, Delft, The Netherlands),
aspergillopepsin I (see Materials & Methods),
Multifect PR 15 L (aspergillopepsin I-like protease from *Trichoderma reesei*; http//biosciences.dupont.com).

The results (cf. FIG. 3), show that the purified Trypsin-Chymotrypsin inhibitor preparation incorporates protein bands with a size of approximately 10 kDa. These data also show that under simulated stomach conditions and in the presence of pepsin and equal amounts of the various proteinases, the *Aspergillus niger* aspergilloglutamic peptidase is most effective in degrading the upper bands present in a purified preparation of Trypsin-Chymotrypsin inhibitors.

Example 9

*Aspergillus niger* Aspergilloglutamic Peptidase Cleaves Alpha Amylase/Trypsin Inhibitors in a Dose Dependent Manner In the present Example we determine the quantity of *A. niger* aspergilloglutamic peptidase enzyme protein required to hydrolyze under simulated stomach conditions the alpha amylase/protease inhibitors present in 1 gram of wheat gluten. To that end gluten from wheat (Sigma) was solubilized in 50 mmol/l citric acid pH 4.0 in a concentration of 9.35 mg/ml. To this thoroughly stirred mixture pepsin enzyme protein was added to reach an end concentration of 0.2 mg/ml and then six one ml samples were taken. To these six samples increasing quantities of pure *A. niger* aspergilloglutamic peptidase enzyme were added. To sample 1: no AGP was added, to sample 2: 0.09 mg, to sample 3: 0.19 mg, to sample 4: 0.28 mg, to sample 5: 0.37 mg and to the last sample: 0.47 mg. The different samples were then incubated for 60 minutes at 37 degrees Celcius and from each sample aliquots for SDS-PAGE analysis were taken at t=0 minutes and t=60 minutes. SDS-PAGE analysis was carried out according to the Invitrogen protocol.

The results (cf. FIG. 4) show that by adding 0.28 mg of pure *A. niger* aspergilloglutamic peptidase the alpha amylase/protease inhibitors present in 9.35 mg of wheat gluten can be hydrolyzed within a one hour period. This implies that 30 mg of pure *A. niger* aspergilloglutamic peptidase (corresponding with 15 000 HPU) can cope with 1 gram of wheat gluten under such simulated gastric conditions. Thus, after the partial fragmentation of alpha amylase/protease inhibitors by an oral *A. niger* aspergilloglutamic peptidase preparation, the newly generated inhibitor peptides will be further degraded to non-immunogenic oligo-peptides by pepsin during stomach passage and, after entering the duodenum, by pancreatic proteases such as trypsin and chymotrypsin.

The invention claimed is:

1. A method of improving animal performance comprising improving feed conversion ratio, and/or improving daily weight gain, and/or reducing intestinal inflammation, and/or reducing nitrogen excretion in an animal fed cereals, pulses, oilseeds, and/or tubers, wherein the method comprises orally administering to an animal in need of improved performance a sufficient amount of the *Aspergillus niger* aspergilloglutamic peptidase.

2. The method according to claim 1, wherein the cereals are selected from the group consisting of wheat, barley and maize, and wherein the pulse is soybean.

3. The method according to claim 1, wherein the animal is a monogastric animal.

* * * * *